United States Patent [19]

Kubo

[11] Patent Number: 4,781,587
[45] Date of Patent: Nov. 1, 1988

[54] DENTAL TREATMENT DEVICE

[76] Inventor: Takeo Kubo, 1091 Konakadai-cho, Chiba-shi, Chiba-ken, Japan

[21] Appl. No.: 872,727

[22] Filed: Jun. 10, 1986

[30] Foreign Application Priority Data

Jun. 17, 1985 [JP] Japan .............................. 60-90185[U]
Jan. 25, 1986 [JP] Japan .................................. 61-13023

[51] Int. Cl.⁴ ............................................ A61C 17/04
[52] U.S. Cl. ...................................................... 433/93
[58] Field of Search ............................. 433/93, 94, 91

[56] References Cited

FOREIGN PATENT DOCUMENTS 1949517  4/1971  Fed. Rep. of Germany ........ 433/93

Primary Examiner—Robert Peshock
Attorney, Agent, or Firm—Frank J. Jordan; C. Bruce Hamburg; Manabu Kanesaka

[57] ABSTRACT

A dental treatment device for protecting a tongue and removing liquid in a mouth comprises an elongated member and a protecting member connected to an end portion of the elongated member. The elongated member includes a hole extending therethroough, and a connecting portion communicating the hole. The connecting portion is connected to a vacuum source for inhaling fluid through the hole. The protecting member includes a body member having a space formed therein for communicating the hole of the elongated member and at least one opening communicating the space, and a first protecting plate connected to the body member. The first protecting plate extends substantially laterally outwardly from an upper portion of the body member so that when the body member is disposed along a side of a tongue, a part of an upper portion of the tongue is covered by the first protecting plate to thereby protect and depress the tongue and the liquid in the mouth is removed through the opening of the body member.

13 Claims, 4 Drawing Sheets

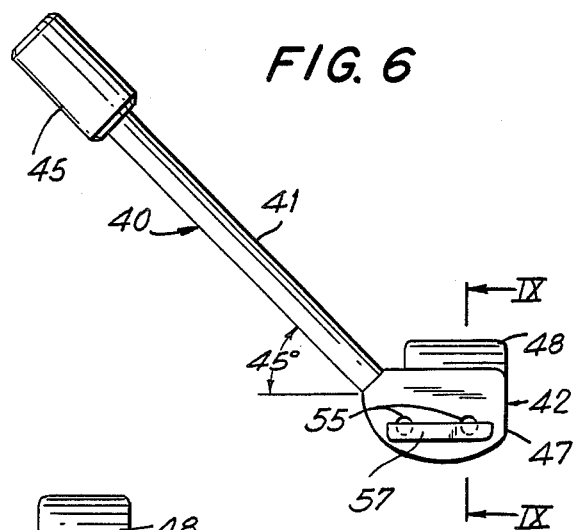
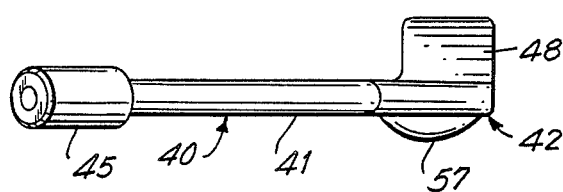
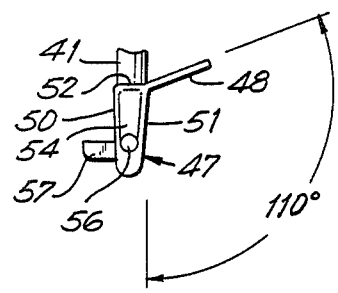
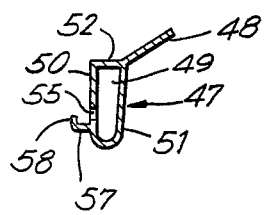
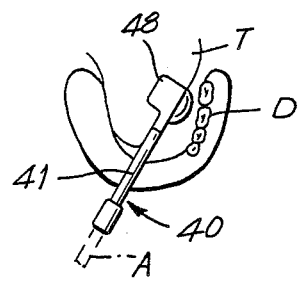

FIG. 13
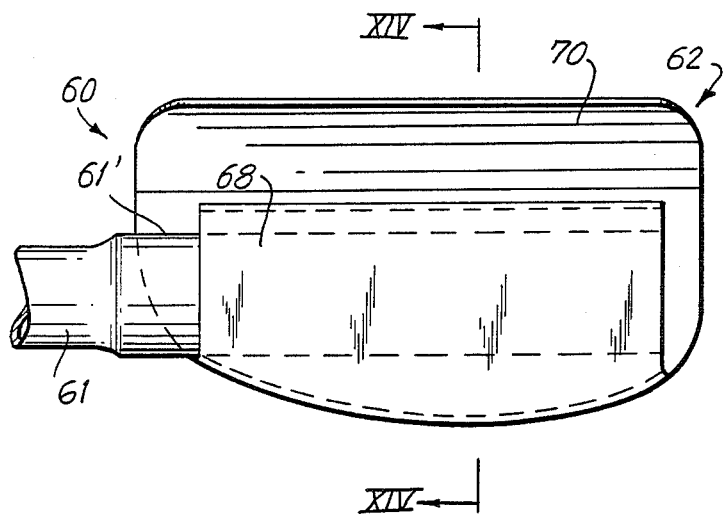
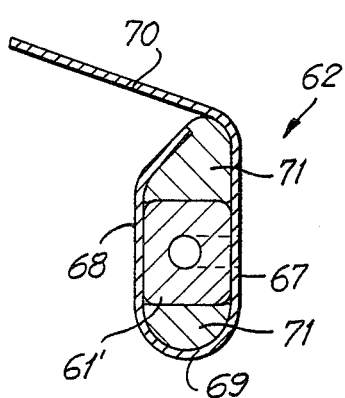
FIG. 14
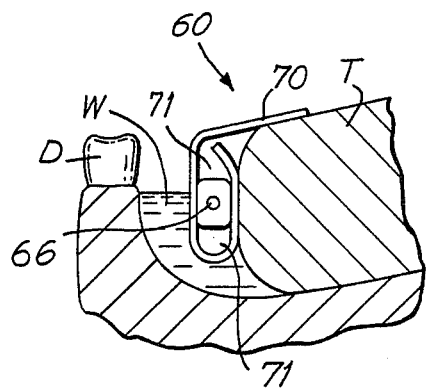
FIG. 15

DENTAL TREATMENT DEVICE

BACKGROUND OF THE INVENTION AND RELATED ART STATEMENT

The present invention relates to a dental treatment device, more particularly a device for protecting a tongue as well as for removing liquid in a mouth when grinding a tooth.

When teeth, especially lower teeth are treated, it is preferable to prevent a tongue from moving in a mouth and to cover at least a part of a tongue for protection thereof. If a tongue is moved in a mouth, the tongue may touch a treatment device, so that the tongue may hurt by the device. Particularly, when lower molar teeth are treated, this tongue protection is required. In this respect, it has been practiced that a dentist holds a tongue of a patient by means of a dental mirror having a holding rod with a mirror. Namely, a dentist manipulates the dental mirror to hold and protect a tongue while treatment of a tooth.

Especially, when a tooth is ground, it is required to press a tongue downwardly to prevent the tongue from being hurt by touching to a grinder. Further, when grinding a tooth by a turbine rotating at a high speed, it is required to cool a tooth to be ground by applying water thereto. Otherwise, the high speed grinding of a tooth causes pain to a patient due to frictional heat between the grinder and the tooth. Also, since cooling water is supplied to a tooth to be ground while grinding, it is necessary to remove the cooling water and saliva from a mouth of a patient.

When a tooth is ground, therefore, a dentist manipulates a dental mirror to hold and protect a tongue while grinding a tooth. Also, cooling water and saliva must be removed from a mouth. Generally, an assistant periodically enter a vacuum pipe into a mouth to remove the liquid.

In the conventional method as explained above, there are several drawbacks. Namely, a tongue can not be securely fixed or held by the dental mirror. Therefore, if a tongue is moved, a tongue may touch a grinder and hurt. Also, a tongue can not be properly covered by the dental mirror. Therefore, it a grinder is inadequately moved in a mouth, the grinder may touch a tongue and other tissues to hurt the same. Further, an assistant must be skilled in manipulating the vacuum pipe. In addition, when grinding a tooth, it is required to insert the grinder, mirror and vacuum pipe into a mouth. Therefore, manipulation of these tools is not easy. Also, insertion of these tools into a mouth makes a patient uncomfortable.

In view of the inconveniences and drawbacks of the conventional tools, the present invention has been made.

Accordingly, one object of the present invention is to provide a dental treatment device for protecting a tongue as well as removing liquid in a mouth.

Another object of the invention is to provide a dental treatment device as stated above, which can be easily manipulated and operated effectively.

A further object of the invention is to provide a dental treatment device as stated above, in which the structure is simple and easily and economically manufactured.

Further objects and advantages of the invention will be apparent from the following description of the invention.

SUMMARY OF THE INVENTION

In accordance with the present invention, there is provided a dental treatment device to protect a tongue and remove liquid in a mouth when grinding a tooth. The dental treatment device comprises an elongated member having a hole extending therethrough, and a connecting portion formed on the elongated member, and a protecting member connected to an end portion of the elongated member. The connecting portion of the elongated member communicates the hole and is adapted to be connected to a vacuum source for inhaling fluid through the hole.

The protecting member includes a body member having a space formed therein for communicating the hole of the elongated member and at least one opening communicating the space, and a first protecting plate connected to the body member. The first protecting plate extends substantially laterally outwardly from an upper portion of the body member so that when the body member is disposed along a side of a tongue, a part of an upper portion of the tongue is covered by the first protecting plate to thereby protect and depress the tongue and the liquid in the mouth is removed through the opening of the body member.

Preferably, the body member of the protecting member includes a plurality of first openings at a tooth side portion opposite the first protecting plate and at least one second opening at a lower side opposite a side where the elongated member is attached. The protecting member may be provided with a second protecting plate extending laterally outwardly from the tooth side portion of the body member. The second protecting plate prevents tissue from raising upwardly when tongue is depressed by the first protecting plate.

In case the dental treatment device of the present invention is used when grinding a tooth, a tongue of a patient is prevented from moving in a mouth and is covered for protection. Further, water and saliva in a mouth of the patient is efficiently removed. Accordingly, when grinding a tooth, it is only required to insert into a mouth of a patient a grinder with a water ejecting nozzle and the dental treatment device of the invention. A dentist can hold and manipulate the grinder and the dental treatment device of the invention by himself without help of an assistant.

BRIEF DESCRIPTION OF THE DRAWINGS

FIG. 6 is a front view of a second embodiment of a dental treatment device of the present invention, which is to be used for treatment of left side teeth of a patient;

FIG. 7 is a plan view of the dental treatment device in FIG. 6;

FIG. 8 is a right side view of the dental treatment device in FIG. 6;

FIG. 9 is a cross section view taken along lines IX—IX in FIG. 6;

FIG. 10 is an explanatory view for showing condition of use of the dental treatment device in FIG. 6;

FIG. 13 is an enlarged rear view of the dental treatment device in FIG. 11;

FIG. 14 is a cross section view taken along lines XIV—XIV in FIG. 13; and

FIG. 15 is an explanatory view for showing condition of use of the dental treatment device of FIG. 11.

DETAILED DESCRIPTION OF PREFERRED EMBODIMENTS

Figure 1:
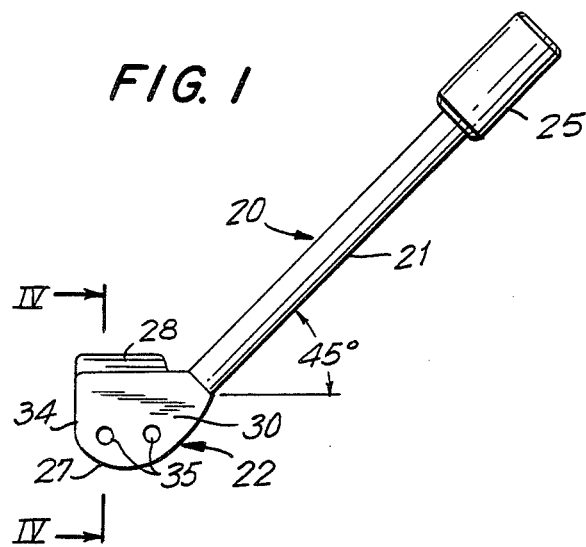
FIG. 1 is a front view of a first embodiment of a dental treatment device ofthe present invention, which is to be used for treatment of right side teeth of a patient.

Referring to the drawings, preferred embodiments of the present invention will be explained.

Figure 2:
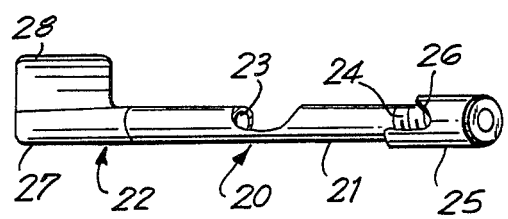
FIG. 2 is a plan view ofthe dental treatment device in FIG. 1, wherein an elongated member is partly cut.
Figure 3:
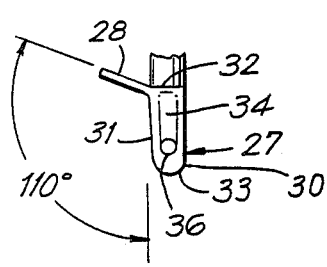
FIG. 3 is a left side view of the dental treatment device in FIG. 1.
Figure 4:
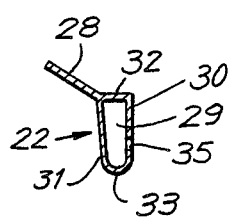
FIG. 4 is a cross section view taken along lines IV—IV in FIG. 1.
Figure 5:
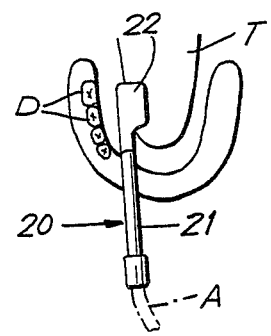
FIG. 5 is an explanatory view for showing condition of use of the dental treatment device in FIG. 1.

FIGS. 1-5 show a first embodiment of the dental treatment device of the invention, which is especially used for treatment of the right side teeth of a patient. As shown in the drawings, a dental treatment device 20 of the invention comprises an elongated member 21, and a protecting member 22 connected to an end of the elongated member 21 at an angle of, for example 45 degrees. The elongated member 21 and the protecting member 22 may be made of a metal, such as a stainless steel, and detachably connected together, or the members 21 and 22 may be made of a plastic material and integrally molded together.

The elongated member 21 is provided with a hole 23 extending throughout the entire length thereof, and outer threads 24 at an upper end. Attached to the upper end of the elongated member 21 is a connecting member 25 having inner threads 26. The inner threads 26 engage the outer threads 24 when the connecting member 25 is fixed to the elongated member 21. Namely, the connecting member 25 operates to connect the elongated member 21 to a vacuum pipe A. The connecting member 25, therefore, may be changed to a different connecting member 25' (not shown) having a different diameter, so that any size of a vacuum pipe A can be securely connected to the elongated member 21 by means of the connecting member 25. The connecting member 25 must be changed to a different connecting member depending on the diameter of the vacuum pipe A to be connected.

The protecting member 22 comprises a body member 27 connected to a lower end of the elongated member 21, and a protecting plate 28. The body member 27 includes a space 29 therein communicating the hole 23 of the elongated member 21 and is formed of a tooth side portion 30, tongue side portion 31, upper portion 32, lower portion 33 and end portion 34. The protecting plate 28 extends outwardly and slightly upwardly from an upper corner of the side portion 31 at an angle, for example 110 degrees. The tooth side portion 30 is provided with two openings 35 at a lower portion thereof, and the end portion 34 is also provided with an opening 36 at a lower portion thereof. The openings 35, 36 communicate the space 29, so that fluid is inhaled from the openings 35, 36 into a vacuum source through the space 29, hole 23 and vacuum pipe A.

The lower portion 33 is curved from a portion adjacent the elongated member 21 to the end portion 34, wherein the end portion 34 is made smaller than the other portions to facilitate insertion of the protecting member 22 into a mouth. Further, the corners of the protecting member 22 are rounded to provide smoothness and softness to a patient when the protecting member 22 is inserted into a mouth.

When the dental treatment device 20 is used for grinding a tooth, a dentist holds the device 20 by one hand and a grinder (not shown) by the other hand. The device 20 is inserted into a mouth of a patient parallel to lower teeth D, so that a part of an upper portion of a tongue adjacent the teeth D is covered by the protecting plate 28 and a side portion of the tongue is covered by the body member 27. Namely, in accordance with the dental treatment device 20 of the present invention, a part of a tongue adjacent a tooth to be ground is properly covered for protection against the grinding of the tooth, and the tongue is immovably retained in the mouth to prevent the tongue from touching to the grinder accidentally.

When the tooth is ground, saliva and water ejected from the grinder for cooling the tooth accumulate inside a mandible. The water and saliva inside the mandible are inhaled through the openings 35, 36 of the body member 27 and the vacuum pipe A to remove the same from the mouth. In the present invention, it is unnecessary to insert a vacuum pipe in a mouth separately in addition to the dental treatment device 20.

Referring to FIGS. 6-10, a second embodiment of a dental treatment device 40 in accordance with the present invention is shown. The dental treatment device 40 is especially used for treatment of the left side teeth of a patient, while the dental treatment device 20 is used for treatment of the right side teeth. The device 40 comprises an elongated member 41, and a protecting member 42 connected to the elongated member 41 at an angle, for example 45 degrees, as in the device 20.

The elongated member 41 is provided with a hole 43 (not shown) extending through the entire length thereof, and a connecting member 45 detachable connected to the end thereof. A vacuum pipe A is connected to the member 45 for inhaling fluid therethrough. The protecting member 42 includes a body member 47, and a protecting plate 48 extending laterally and slightly upwardly from an upper corner of a tongue side portion 51 of the body member 47 at an angle, for example 110 degrees. The body member 47 includes openings 55 at a tooth side portion 50, and an opening 56 at an end portion 54, the openings 55, 56 communicating a space 49 inside the body member 47.

In the device 40, the tooth side portion 50 is provided with a plate 57 extending laterally outwardly therefrom parallel to an upper portion 52. The plate 57 is located below the opening 55 and includes an outer flange 58 at an outer periphery thereof. The plate 57 is designed to prevent tissue from raising upwardly in a mouth especially when the tongue is depressed strongly by the device 40. The device 20 may be provided with the plate 57.

When the dental treatment device 40 is used, the device 40 is inserted into a mouth parallel to teeth D. Since the device 40 is provided with the plate 57, even if a tongue is pushed away from the left side teeth and is depressed downwardly, the tissue under the tongue adjacent the left side teeth does not raise upwardly. A tooth can be ground in this condition. In the dental treatment device 40, the tissue under the tongue is also protected by the device 40.

Figure 11:
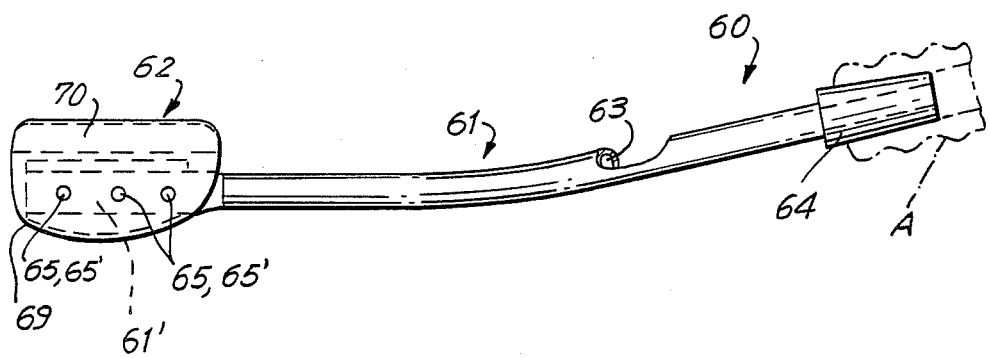
FIG. 11 is a partly cut front view of a third embodiment of a dental treatment device of the present invention, which is to be used for treatment of right side teeth of a patient.
Figure 12:
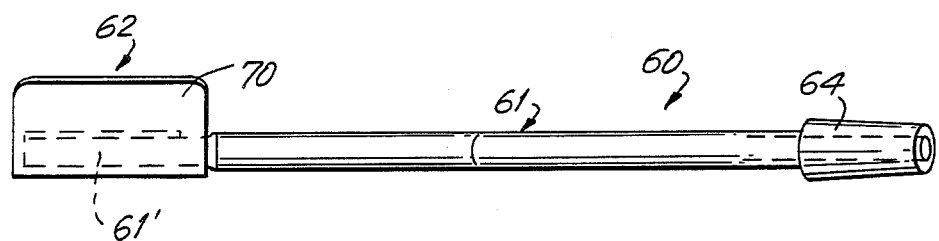
FIG. 12 is a plan view of the dental treatment device in FIG. 11.

FIGS. 11-15 show a third embodiment of a dental treatment device 60 of the present invention, which is designed for treatment of the right side teeth. The device 60 comprises an elongated member 61 and a protecting member 62 connected to a front portion of the elongated member 61.

The elongated member 61 is provided with a hole 63 extending throughout the entire length thereof, and a connecting member 64 detachably connected to a rear end thereof. The connecting member 64 is connected to a vacuum pipe A for inhaling fluid through the hole 63. Also, the elongated member 61 includes three openings 65 at a front portion 61′, and an opening 66 at a front end thereof, the openings 65, 66 communicating the hole 63.

The protecting member 62 is made of a single plate covering the front portion 61′ of the elongated member 61. The protecting member 62 is formed of a tooth side portion 67, a tongue side portion 68, a lower portion 69 and a protecting plate 70 extending slightly upwardly toward the tongue side portion 68 from an upper end of the tooth side portion 67. The front portion 61′ is securely retained between the tooth side portion 67 and the tongue side portion 68. As shown in FIG. 14, spaces between the protecting member 62 and the front portion 61′ are filled with a filling material 71 so that the protecting member 62 can be immovably connected to the front portion 61′.

The tooth side portion 67 of the protecting member 62 is provided with three openings 65′ communicating the openings 65. Therefore, fluid is inhaled into the hole 63 through the openings 65, 65′ and 66.

When the dental treatment device 60 is used, the device 60 is inserted into a mouth parallel to teeth D and is arranged so that a part of a tongue is covered by the protecting member 62. The tongue is protected and retained by the protecting member 62. Further, water and saliva W accumulating in a mouth when grinding a tooth are removed by the device 60.

The dental treatment device 60 is designed for treatment of the right side teeth of a patient. When the left side teeth of a patient is treated, it is necessary to use a dental treatment device similar to the device 60, wherein the protecting plate 70 and the openings 65, 65′ are located on the tongue side and the teeth side, respectively.

In accordance with the present invention, the elongated member and the protecting member may be integrally formed by means of a plastic material and detachably connected to the vacuum pipe. In this case, the dental treatment device may be thrown away in single usage, so that the dental treatment device need not be cleaned in each time. On the other hand, the elongated member may be securely connected to an end of the vacuum pipe A, and the protecting member may be detachably connected to the elongated member.

As explained above, especially when a tongue side of a lower molar tooth is treated or ground, the dental treatment device of the present invention can protect a tongue and retain the same to prevent moving in a mouth. At the same time, saliva and water for cooling a tooth when grinding can be removed from a mouth.

In the conventional method, skill and careful attention are required for grinding a tongue side of a lower molar tooth, so that a treatment of the lower molar tooth is one of difficult treatments. However, in the device of the present invention, a tongue can be protected and securely retained in a mouth. Consequently, a dentist can treat a tooth easily for a short period of time. Also, it is comfortable for a patient because no special vacuum pipe is inserted into a mouth.

The dental treatment device of the present invention is especially useful for grinding a tongue side of a lower molar tooth. However, the dental treatment device of the invention can be used for other purposes, such as surgical treatment of a tongue side of a lower molar tooth (including surgical treatment due to periodontal diseases and implant); cutting a tooth for extraction thereof (lower molar); and other treatments of teeth.

The invention has been explained with reference to the specific embodiments of the invention, the explanation is illustrative and the invention is limited only by the appended claims.

I claim:

1. A dental treatment device adapted for protecting a tongue and removing liquid in a mouth, comprising:
    an elongated member extending substantially linearly and having a hole extending throughout the entire length of the elongated member, a connecting portion formed at one end of the elongated member, said connecting portion communicating said hole and adapted to be connected to a vacuum source for inhaling fluid through the hole, and an end portion formed at the other end of the elongated member for communicating said hole, and
    a protecting member connected to the end portion of the elongated member to incline diagonally relative to the elongated member, said protecting member including a body member having upper, lower, tongue side and tooth side portions, a space formed inside the body member for communicating the hole of the elongated member and at least one opening at a lower portion of the body member for communicating between said space and outside, and a first protecting plate in the rectangular form, said first protecting plate being connected to the body member to extend substantially laterally outwardly from the upper portion of the body member in the direction away from the tongue side portion of the body member so that when the body member is, in use, disposed between teeth and a tongue, a part of an upper portion of the tongue is covered by the first protecting plate to thereby protect and hold the tongue, liquid in the mouth being removed through the opening and space of the body member and the hole of the elongated member.

2. A dental treatment device according to claim 1, in which said body member of the protecting member includes a plurality of first openings at the tooth side portion opposite the first protecting plate and at least one second opening at a lower side opposite a side where the elongated member is attached.

3. A dental treatment device according to claim 2, in which said protecting member further includes a second protecting plate extending laterally outwardly from the tooth side portion of the body member, said second protecting plate preventing tissue from raising upwardly when tongue is depressed by the first protecting plate.

4. A dental treatment device according to claim 3, in which said second protecting plate is attached to the body member below the first openings.

5. A dental treatment device according to claim 4, in which said lower portion of the body member of the protecting member is slightly curved along the longitudinal direction thereof.

6. A dental treatment device according to claim 5, in which said protecting member is integrally formed of a plastic material.

7. A dental treatment device according to claim 5, in which said first protecting plate extends rightwardly from the body member when viewing the protecting member from a side of the elongated member for protecting a right side of a tongue of a patient.

8. A dental treatment device according to claim 5, in which said first protecting plate extends leftwardly from the body member when viewing the protecting member from a side of the elongated member for protecting a left side of a tongue of a patient.

9. A dental treatment device according to claim 2, in which said body member of the protecting member is integrally formed with the elongated member.

10. A dental treatment device according to claim 9, in which said first protecting plate includes a covering situated over the body member so that the first protecting plate is securely connected to the body member.

11. A dental treatment device according to claim 10, in which said elongated member and the protecting member are integrally formed of a plastic material.

12. A dental treatment device adapted for protecting a tongue and removing liquid in a mouth, comprising:
an elongated member extending substantially linearly and including a hole extending throughout the entire length of the elongated member, a connecting portion formed at one end of the elongated member, said connecting portion communicating said hole and adapted to be connected to a vacuum source for inhaling fluid through the hole, and an end portion formed at the other end of the elongated member for communicating said hole, and
a protecting member connected to the end portion of the elongated member to incline diagonally relative to the elongated member, said protecting member including a body member having upper, lower tongue side and tooth side portions, a space formed inside the body member for communicating the hole of the elongated member and at least one opening at a lower portion of the body member for communicating between said space and outside, a first protecting plate in the rectangular form, said first protecting plate being connected to the body member to extend substantially laterally outwardly from the upper portion of the body member in the direction away from the tongue side portion of the body member so that when the body member is, in use, disposed between teeth and a tongue, a part of an upper portion of the tongue is covered by the first protecting plate to thereby protect and hold the tongue, liquid in the mouth being removed through the opening and space of the body member and the hole of the elongated member, and a second protecting plate extending laterally outwardly from the tooth side portion of the body member, said second protecting plate preventing tissue from raising upwardly when a tongue is depressed by the first protecting plate.

13. A dental treatment device according to claim 12, in which said body member includes a plurality of openings at the tooth side portion, said second protecting plate being attached to the body member below the openings.

* * * * *